United States Patent [19]

Ryer et al.

[11] 4,116,643

[45] Sep. 26, 1978

[54] AMINE SALTS OF CARBOXYLATE HALF ESTERS OF 1-AZA-3,7-DIOXABICYCLO [3.3.0] OCT-5-YL METHYL ALCOHOLS, THEIR PREPARATION AND USE AS ADDITIVES FOR GASOLINE AND MIDDLE DISTILLATE FUELS

[75] Inventors: Jack Ryer, East Brunswick; Stanley J. Brois, Westfield; Esther D. Winans, Colonia, all of N.J.

[73] Assignee: Exxon Research & Engineering Co., Linden, N.J.

[21] Appl. No.: 814,161

[22] Filed: Jul. 11, 1977

Related U.S. Application Data

[60] Continuation-in-part of Ser. No. 752,872, Dec. 20, 1976, which is a division of Ser. No. 573,545, May 1, 1975, Pat. No. 4,017,406.

[51] Int. Cl.$^2$ ................................................ C10L 1/22
[52] U.S. Cl. ........................................ 44/63; 252/392; 252/394; 44/71
[58] Field of Search ................... 44/63, 71; 252/392, 252/394; 260/307 F

[56] References Cited

U.S. PATENT DOCUMENTS

| 3,455,831 | 7/1969 | Davis | 252/51.5 A |
|---|---|---|---|
| 3,455,832 | 7/1969 | Davis | 252/51.5 A |
| 4,035,309 | 7/1977 | Brois | 44/68 |

*Primary Examiner*—Winston A. Douglas
*Assistant Examiner*—Y. Harris-Smith
*Attorney, Agent, or Firm*—Roland A. Dexter

[57] ABSTRACT

Amine salts of carboxylate half esters of 1-aza-3,7-dioxabicyclo [3.3.0] oct-5-yl methyl alcohols which are the reaction products of organic acid materials, preferably long chain dicarboxylic anhydrides such as octadecenyl and polyisobutenylsuccinic anhydrides and aldehyde/-tris [hydroxymethyl]aminomethane (THAM) adducts or mixtures are anti-rust additives for hydrocarbon fuels, such as gasoline and middle distillates.

11 Claims, No Drawings

AMINE SALTS OF CARBOXYLATE HALF ESTERS OF 1-AZA-3,7-DIOXABICYCLO [3.3.0] OCT-5-YL METHYL ALCOHOLS, THEIR PREPARATION AND USE AS ADDITIVES FOR GASOLINE AND MIDDLE DISTILLATE FUELS

CROSS-REFERENCE TO RELATED APPLICATIONS

This application is a continuation-in-part of U.S. patent application Ser. No. 752,872 filed Dec. 20, 1976 which is a Divisional application of U.S. patent application Ser. No. 573,545 filed May 1, 1975, now issued as U.S. Pat. No. 4,017,406.

BACKGROUND OF THE INVENTION

1. Field of the Invention

The invention relates to novel oil-soluble amine salts of partial esters derived from the reaction of organic acid materials such as dicarboxylic acids or anhydrides and an aldehyde/tris-(hydroxymethyl) aminomethane adduct or mixture. These novel oil-soluble amine salts have utility as additives for hydrocarbon fuels including gasoline.

2. Description of Prior and Related Art

Lubricant and fuel additives derived from hydrocarbon substituted succinic anhydride, e.g., polyisobutenylsuccinic anhydride, with compounds containing both an amine group and a hydroxy group have been suggested or investigated in the prior art. The art also teaches useful lubricating oil detergents of the Schiff base type are prepared by reacting alkenylsuccinic acid anhydride and a polyamine to provide an imide intermediate subsequently reacted with an aldehyde (see U.S. Pat. No. 3,455,831). United Kingdom Specification No. 809,001 teaches corrosion inhibitors comprising a multiple salt complex derived from the reaction product of hydrocarbyl substituted dicarboxylic acids and hydroxy amines (including 2-amino-2-methyl-1,3-propane-diol [AMP] and tris hydroxy methylaminomethane (hereafter designated THAM) further complexed with mono- and polycarboxylic acids.

U.S. Pat. No. 3,632,511 teaches reacting polyisobutenylsuccinic anhydride with both a polyamine and a polyhydric alcohol including THAM. United Kingdom Specification No. 984,409 teaches ashless, amide/imide/ester type lubricant additives prepared by reacting an alkenylsuccinic anhydride, with a hydroxy amine including THAM.

In British Pat. No. 564,506, the condensation product of THAM and formaldehyde, i.e. 1-aza-3,7-dioxabicyclo[3.3.0]oct-5-yl methyl alcohols is said to react with fatty acids to give unstable ester products which are useful as drying oils.

In contrast to the above disclosures, we have found that carboxylic acids or anhydrides can be treated with an aldehyde-THAM adduct or mixture to give novel amine salt compositions particularly useful as an antirust additive for liquid hydrocarbon fuels.

SUMMARY OF THE INVENTION

It has now been discovered that novel hydrocarbon soluble amine salts of partial, i.e. half, esters of 1-aza-3,7-dioxabicyclo[3.3.0]oct-5-yl methyl alcohols can be formed from the product of the reaction of organic dicarboxylic acids and anhydrides, with an aldehyde-(THAM) adduct or aldehyde-(THAM) mixture. For liquid hydrocarbon fuel compositions wherein the amine salt-ester compositions of the invention have been found to be highly useful as anti-rust additives, e.g. in gasoline or middle distillates the carbon chain length is preferably from about $C_8$ to about $C_{50}$ to carbon atoms.

DICARBOXYLIC ACID MATERIALS

Numerous types of acid materials can be utilized according to this invention, however, dicarboxylic acids which afford liquid hydrocarbon fuel soluble amine salt-esters from aldehyde/THAM adducts or mixtures are preferred. Especially preferred reactants are aliphatic substituted succinic acid anhydrides.

Any 2-alkyl, 2-alkenyl-2,3-dialkyl or 2,3-cycloalkenyl substituted dicarboxylic acid material, i.e. acid, anhydride or ester e.g., succinic acid anhydride or its corresponding acid, or mixtures thereof can be used in the present invention. The alkyl or alkenyl group can be branched or straight chain, and there is no real upper limit to the number of carbon atoms therein.

It is particularly preferred that the aliphatic substituent in the 2-position of the succinic anhydride is a polymer of $C_2$ to $C_5$ monoolefins, e.g., ethylene, propylene, butylene, isobutylene and pentene. The polymers can be homopolymers such as polyisobutylene and styrene as well as copolymers of two or more of monoolefins such as copolymers of ethylene and propylene, butylene and isobutylene or of propylene and isobutylene.

The polymers will have average molecular weights within the range of about 50 to about 100, or more usually between about 80 and about 800. Particularly useful olefin polymers have average molecule weights within the range of about 200 and about 1000 with approximately one double bond per polymer chain.

An especially valuable starting material for a highly potent dispersant additive made in accordance with this invention is polyisobutylene having an average molecular weight in the range of about 600 to about 800. Molecular weights are conveniently determined by vapor phase osmometry; said determinations being used for all values set forth herein.

The substituted succinic anhydrides are readily available from the reaction of maleic anhydride with polyolefins or with chlorinated polyolefins. Interaction of polyolefins with maleic anhydride [ene reactions] give polyalkenylsuccinic anhydrides. The olefin polymer can, if desired, be first halogenated, for example, chlorinated or brominated to about 2 to 5 wt.% chlorine, or about 4 to 8 wt.% bromine, based on the weight of polymer, and then reacted with the maleic anhydride.

Other halogenation techniques for attaching the dicarboxylic acid material to a long hydrocarbon chain, involve first halogenating the unsaturated dicarboxylic acid material and then reacting with the olefin polymer, of by blowing halogen gas, e.g., chlorine, through a mixture of the polyolefin and unsaturated dicarboxylic acid material, then heating to 150° to 220° C. in order to remove HCl gas.

In summary therefore, the dicarboxylic acid material used in the invention includes alpha-beta unsaturated $C_4$ to $C_{10}$ dicarboxylic acid or anhydrides or esters thereof such as fumaric acid, itaconic acid, maleic acid, maleic anhydride, malic acid, maleamic acid, chloromaleic acid, dimethyl fumarate, etc. These dicarboxylic acid materials are substituted with a hydrocarbon chain containing at least about 2 carbons to more than 50 carbons, preferably from about 8 to about 50 depending upon the nature of composition into which the additive will be incorporated, that is, for oleaginous compositions such as gasoline and middle distillate fuels, the carbon chain length ranges from 8 to 50 carbons.

As earlier stated, numerous acids can be reacted with aldehyde/THAM adducts or mixtures. These acids are illustrated by the following types: aromatic acids such as phthalic, mellitic and pyromellitic; and, thio acids such as tridecanethionothiolic.

ALDEHYDE-THAM ADDUCTS

The requisite aldehyde/THAM adducts, more specifically 1-aza-3,7-dioxabicyclo[3.3.0]oct-5-yl methyl alcohols (I), can be readily prepared by condensing two moles of aldehyde with one mole of THAM (Equation 1) according to the procedures described by M. Senkus in the "Journal of the Americal Chemical Society", 67, 515 (1945).

Equation 1

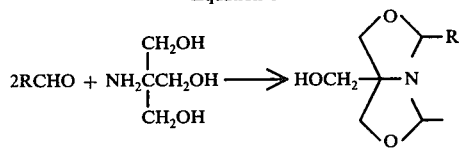

R = H, CH$_3$, n-C$_3$H$_7$, n-C$_3$H$_{11}$, Ph, PhCH$_2$, etc. Thus, a variety of aldehydes such as formaldehyde, acetaldehyde, propionaldehyde, butyraldehyde, isobutyraldehyde, 2-ethylhexanal, dodecyl aldehyde, benzaldehyde, tolualdehyde, anisaldehyde, piperonal, naphthaldehydes, phenylacetaldehyde, furfural, etc., can be condensed with (THAM) to produce symmetrically substituted (I, R = R) aldehyde/THAM adducts.

UNSYMMETRICAL ADDUCTS

In another embodiment of the present invention, unsymmetrical adducts may be prepared by first treating THAM with one mole of an aldehyde or ketone (Equation 2) to generate an oxazolidine product (II) according to procedures described in the literature by E. D. Bergmann, "Chemical Reviews", 53, 309 (1953).

Equation 2

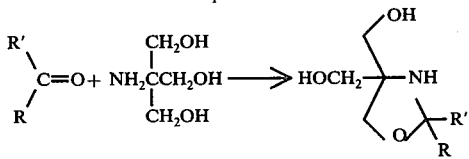

Subsequent treatment of the oxazolidine with a mole of aldehyde affords the unsymmetrical adduct III, as depictured in Equation 3.

Equation 3

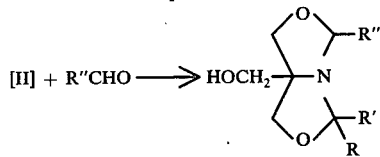

Aldehyde reactants described in the preparation of symmetrically substituted adducts (I) above are suitable for the reactions described in Equations 2 and 3.

Numerous types of ketone reactants can be employed in the formation of the oxazolidines (Equation 2) required in the design of unsymmetrically substituted 1-aza-3,7-dioxabicyclo[3.3.0]oct-5-yl methyl alcohols (III). Included in the repertory of useful ketones are acetone, butanone, pentanones, methyl isobutyl ketone, pinacolone, amyl methyl ketone, cyclopentanone, cyclohexanone, acetophenone, etc.

Long chain aldehydes and ketones formed in the oxidation of copolymers of ethylene and propylene, butylene and isobutylene, and ethylene, propylene and 1,4-hexadiene can also be employed. The aldehyde and ketone functionalized polymers will have average molecular weights within the range of about 500 to about 100,000.

In forming unsymmetrical adducts (III) from oxazolidine generated from ketone reactants, a particularly preferred aldehyde is formaldehyde which, owing to its favorable steric requirements, rapidly cyclizes the oxazolidine intermediate to the desired bicyclic structure, III (R'=H).

REACTION CONDITIONS FOR HALF ESTER FORMATION

The formation of the intermediate esters of the present invention can be effected by reacting a mole of dicarboxylic acid anhydride with a mole of an aldehyde/THAM adduct i.e. equimolar as portrayed in Equation 4.

Equation 4

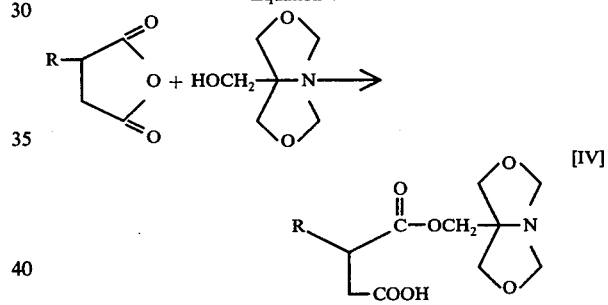

The mode of addition of reactants does not appear to affect product composition, and convenience will usually dictate which reagent is added to the other. Zinc salts such as zinc acetate, chloride, etc. when required, can be employed to catalyze the esterification process. In general, the reaction is effected in a reactor in the absence of or presence of an inert diluent such as xylene and solvent oil and heating the mixture from about 50° C. to about 230° C. preferably 70° C. to 150° C. for about 10 minutes to 48 hours, more preferably 1 to 3 hours. Completion of reaction can be readily discerned by infrared analysis.

The disappearance of the characteristic anhydride carbonyl absorption bands, together with the presence of strong ester and carboxylic acid carbonyl bands indicate that complete esterification has occurred.

In another embodiment of the present invention, the preparation of half ester intermediates can be sometimes achieved by simply combining the carboxylic acid or anhydride reactant with a mixture of aldehyde and THAM in the proper molar proportions and heating the well-mixed reagents (neat or in diluent) at about 80° C. to about 200° C. for about 1–24 hours, or until infrared analyses of the mixture indicate that product formation is complete. In such instances, particularly with formaldehyde as reactant, the rate of aldehyde/THAM adduct formation apparently is quite rapid in the presence of the carboxylic acid reactant which at some point, undergoes interaction with the aldehyde/THAM adduct to generate the desired ester.

In a preferred embodiment of the present invention, the symmetrical adduct can be formed in situ, by heating a mixture of 2 moles of aldehyde and a mole of THAM at about 80° C. to about 210° C. for about 1 to about 4 hours. Quite often infrared analysis can be used to discern complete reaction by the disappearance of the aldehyde carbonyl absorption bond. In instances where unsymmetrical adducts are desired, a mole of aldehyde or ketone is heated with a mole of THAM at about 80° C. to about 210° C. for about 1 to about 24 hours, or until periodic infrared analyses of the reaction mixture show the absence of a carbonyl absorption band. Thereafter, a mole equivalent of aldehyde, preferably formaldehyde is added to the intermediary oxazolidine and the mixture is heated at about 80° C. to about 210° C. for approximately 1 to about 4 hours. The in situ formed adduct can thereafter be reacted with a carboxylic acid or anhydride by adding, for example, a mole of alkenylsuccinic anhydride to the adduct and heating the well-stirred reaction mixture at about 80° C. to about 200° C. for approximately 15 minutes to about 4 hours, or until the infrared spectrum of the reaction mixture reveals the absence of the characteristic anhydride carbonyl absorption bands.

AMINE SALTS OF CARBOXYLATE HALF ESTERS OF 1-AZA-3,7-DIOXABICYCLO[3.3.0]OCT-5-YL METHYL ALCOHOLS

The amines useful for preparation of the amine salts of the invention are of the group consisting essentially of hydroxy amines of the formula

HO—(CH$_2$)$_n$NR$_1$R$_2$ wherein $n$ represents the whole number 2, 3 or 4, R$_1$ and R$_2$ may be the same or different and represent hydrogen, a hydroxy alkyl group having 2 to 4 carbons or an alkyl group having 2 to 4 carbons; and alkylene polyamines of the class consisting of ethylene diamine and diethylene triamine.

The amine salts are readily prepared by mixing together in any suitable inert solvent, preferably a liquid hydrocarbon, such as benzene, one molar equivalent of said partial ester based upon the carboxylic acid group with one molar equivalent of ethanolamine. Thus one mole of half ester is reacted with one mole of hydroxy amine whereas two moles of half ester are reacted with one mole of ethylene diamine and three moles of the half ester are reacted with one mole of diethylene triamine.

The salt formation is substantially instantaneous by admixing in the inert solution, (tetrahydrofuran) however, the formation is usefully carried out at from 32° C. to 80° C., preferably from 25° C. to 60° C., for 0.2 to 10 hours, preferably 2 to 8 hours. There is no need to carry out the preparation under pressure. This makes it possible to conduct the process of the invention in an open vessel in the presence of air or inert gas.

Although not fully understood, the antirust activity of the amine salts appears to be the consequence of the chelate structure inherent in said amine salts.

The following preparations and examples are included herein as further description and illustrative of the present invention.

PREPARATION OF ALDEHYDE-THAM ADDUCTS

Example 1

0.1 mole (12.1 g) of THAM was dissolved in an equal weight of water. To the resulting solution in a 250 ml Erlenmeyer flask equipped with magnetic stirrer was added 0.2 mole (6.0 g) of paraformaldehyde. The stirred mixture was heated to 70° C. to effect dissolution of the paraformaldehyde and continued for 15 minutes at 70 C. to produce the 1-aza-3,7-dioxabicyclo[3.3.0]oct-5-y methyl alcohol (hereinafter called DOBO) in quantitative yields. The product after evaporation of water and recrystallization from benzene melted at 60°-61° C. and analyzed for 49.12% carbon, 7.52% hydrogen and 9.59% nitrogen.

ESTERIFICATION OF ALDEHYDE-THAM ADDUCTS

Example 2

HALF ACID ESTER OF 1-DIOXABICYCLO[3.3.0]OCT-5-YL METHYL OCTADECENYL SUCCINATE 0.5 mole of octadecenylsuccinic anhydride was added to a 1 liter round bottom flask and heated to 140° C. for an hour to convert any partially hydrolyzed reactant to the anhydride form. After cooling the nitrogen-blanketed reactor to 100° C., 0.5 mole of DOBO was added in one portion. The alcohol reagent readily dissolved and the clear solution was heated to 174° C. for about 2 hours. Infrared analysis showed that esterification was complete at this point. The infrared spectrum of the tan product featured prominent absorption bands at 5.75 5.85, 8.65, 9.10, 10.3 and 10.7 microns.

Analysis based on C$_{28}$H$_{50}$NO$_6$: Calculated: C, 67.70 H, 10.15; N, 2.82. Found: C, 66.57; H, 9.95; N, 2.60.

The product, recrystallized from hexane, melted a 58°-62° C.

Example 3

HALF ACID ESTER OF 1-AZA-3,7-DIOXABICYCLO[3.3.0]OCT-5-YL METHYL POLYISOBUTYLENESUCCINATE 0.2 mole (267 g) of polyisobutenylsuccinic anhydride of MW 980 with a Sap. No. of 84 was charged into a liter flask and heated to 180° C. The anhydride reactant is heated at 180° C. under high vacuum for 2 hours to remove any light ends. About 2.8 g of volatiles were collected in a dry ice-cooled receiver. The stirred reactant is then cooled to 120° C., and 0.2 mole (29.0 g) of DOBO plus 1 gram of zinc acetate catalyst are added The stirred reaction mixture is then heated at 210° C. for several hours until infrared analysis shows complete esterification. An equal weight of neutral oil (S-150N) is added to the product at about 120° C. The diluted product analyzed for 0.42% nitrogen and featured an infra red spectrum with a dominant absorption band at 5.7 microns.

Example 4

HALF ACID ESTER OF 1-AZA-3,7-DIOXA-2,8 DI-N-PROPYLBICYCLO[3.3.0]OCT-5-YL METHYL OCTADECENYL-SUCCINATE 0.27 mole of (94.5 g) of normal octadecenylsuccinic anhydride was added to a 500 ml flask and heated for an hour at 140° C. to convert any partially hydrolyzed reactant to the anhydride form. The reaction was cooled to 70° C. and 0.3 mole (68.7 g) of 1-aza-3,7-dioxa-2,8-di-n-propylbicyclo[3.3.0]oct-5-yl methyl alcohol was added to the flask and heating was maintained for 1 hour at 98°–104° C. The I.R. spectrum of the product showed disappearance of anhydride bands and the appearance of 2 bands at 5.75 and 5.85 microns.

Example 5

HALF ACID ESTER OF 1-AZA-3,7-DIOXA-2,8-DIPHENYLBICYCLO[3.3.0]OCT-5-YL METHYL OCTADECENYLSUCCINATE 0.27 mole (94.5 g) of n-octadecenylsuccinic anhydride was added to a 500 ml. flask and heated for an hour at 140° C. The reaction was cooled to 70° C. and 0.30 moles (89.1 g) of 1-aza-3,7-dioxa-2,8-diphenylbicyclo[3.3.0]oct-5-yl methyl alcohol was added to the flask and heating continued for 1 hour at 107°–114° C. The I.R. spectrum of the product showed the appearance of 2 bands at 5.75 and 5.85 microns.

Example 6

HALF ACID ESTER OF 1-AZA-3,7-DIOXABICYCLO[3.3.0]OCT-5-YL METHYL TETRAPROPENYLSUCCINATE 0.8 mole (212.8 g) of tetrapropenylsuccinic anhydride was combined with 0.8 mole (116 g) of DOBO in a 1 liter flask and heated to 138° C. for 2 hours. The product analyzed for 3.2% nitrogen. The calculated value is 3.4%. The I.R. spectrum of the product shows a broad band at about 5.8 microns.

Example 7

HALF ACID ESTER OF 1-AZA-3,7-DIOXA-2,8-DI-N-PROPYLBICYCLO[3.3.0]OCT-5-YL METHYL TETRAPROPENYLSUCCINATE 0.3 mole (79.8 g) of tetrapropenylsuccinic anhydride was reacted with 0.3 mole (68.7 g) of 1-aza-3,7-dioxa-2,8-di-n-propyl-bicyclo[3.3.0]oct-5-yl methyl alcohol in a 500 ml flask at 100° C. for 2 hours. The weight percent nitrogen in the product was 2.81%. The calculated value was 2.83%. The I.R. spectrum of the product showed 2 bands, at 5.75 and 5.85 microns.

Example 8

HALF ACID ESTER OF 1-AZA-3,7-DIOXA-2,8-DIPHENYL-BICYCLO[3.3.0]OCT-5-YL METHYL TETRAPROPENYLSUCCINATE 0.2 mole (53.2 g) of tetrapropenylsuccinic anhydride was combined with 0.2 mole (59.4 g) of 1-aza-3,7-dioxa-2,8-diphenyl-bicyclo[3.3.0]oct-5-yl methyl alcohol in a 500 ml flask and heated to 100°–106° C. for 2 hours. The I.R. spectrum of the product showed 2 bands at 5.75 and 5.85 microns.

Example 9

HALF ACID ESTER OF 1-AZA-3,7-DIOXABICYCLO[3.3.0]OCT-5-YL METHYL n-DODECENYLSUCCINATE 0.25 mols (66.8 g) of n-dodecenylsuccinic anhydride was heated at 160°–180° C. for 3 hours with a nitrogen sparge to dehydrate any acid present. It was then cooled to 90° C. and 0.25 moles (38 g) of DOBO in octane was added and the mixture heated 1 hour at 90° C.–110° C. The product showed no anhydride bands in the I.R. spectrum at 5.4 and 5.6 microns and contained 3.7 wt.% nitrogen.

The following example teaches the formation of products via the reaction of an unsymmetrical adduct formed by successive additions of molar amounts of ketone and aldehyde to THAM followed by esterification of the adduct with succinic anhydride.

Example 10

A quarter mole of THAM was combined with a half mole of cyclohexanone and the mixture heated at reflux until a clear solution was obtained. The solid product which formed on cooling the solution, was recrystallized from boiling toluene. The dried product, melted at 119°–120° C. and was found to be desired cyclohexanone/THAM adduct, i.e., 2-spiro-(cyclohexyl)-4,4-bis(hydroxymethyl)-oxazolidine. Thirty grams (0.149 mole) of the cyclohexanone/THAM adduct and 5 g (0.166 mole) of paraformaldehyde were added to 150 ml of toluene and the mixture was refluxed in a reactor equipped with a Dean-Stark moisture trap. After 2 hours, approximately 3.1 mole of water were collected and reaction was terminated. Removal of solvent and low ends from the reaction mixture by evaporation afforded 32.1 g of crude product which was homogeneous by gas chromatography. Vacuum distillation gave a colorless viscous liquid which boiled at 159°–160° C. (1.0 mm) and featured infrared and nmr spectra consistent with the unsymmetrical adduct, 1-aza-3,7-dioxa-2-spiro-(cyclohexyl)-5-hydroxymethylbicyclo[3.3.0]octane.

Treatment of 0.1 mole of the unsymmetrical adduct with 0.1 mole of succinic anhydride gave the expected half acid-ester product in high yield.

The above examples teach the preparation of the products of the present invention via the reaction of a carboxylic acid or anhydride, preferably the latter, with a discrete aldehyde/THAM adduct, which is first isolated, purified and characterized (if required) and then employed in a second step involving the esterification of a suitable carboxylic acid or anhydride reagent by the adduct alcohol.

We have also discovered that in certain instances, other synthetic options were also effective and oftimes more convenient in preparing the products of the present invention. One approach involves the addition of a carboxylic acid or anhydride to an aldehyde/THAM adduct which is formed in situ, by simply heating the aldehyde and THAM reagents together as illustrated in Example 12.

Example 11

HALF ACID ESTER OF 1-AZA-3,7-DIOXABICYCLO[3.3.0]OCT-5-YL METHYL n-OCTENYLSUCCINAMATE

In a typical reaction, 2 moles (60 g) of paraformaldehyde is added to 1 mole (121 g) of (THAM) and gradually heated with stirring to about 110° C. Heating is continued at 110°–120° C. until a clear solution was obtained. After stirring for 15 minutes, a mole of n-octenylsuccinic anhydride is added to the reactor which is maintained at about 120° C. After the addition of n-octenylsuccinic anhydride is completed, the clear solution is stirred at 120°–130° C. until infrared analysis shows the absence of anhydride bands, e.g. for from about 15 to 30 minutes. Reaction times of 0.25–1 hours, e.g. 15–30 minutes, at 130°–140° C. are sufficient to produce the desired ester derivative.

TABLE I-continued

| Additive of Example | Amine Salt | Concentration Pounds/ Thousand Barrels | NACE Rating |
|---|---|---|---|
| — | OSA.DOBO.HTA | 1.0 | D |

Primene 81R = Branched $C_{18}$ alkyl primary amine sold by Rohm & Haas of Philadelphia, PA.
HTA is a hydrogenated tallow amine reacted with OSA.DOBO (1:1).

MIDDLE DISTILLATE ADDITIVE

The products of Examples 14A and 15 were tested for their effectiveness in two different middle distillate fuels. Also included for comparison are tests of the same middle distillates treated with several commercially available gasoline anti-rust agents. Each additive was first dissolved in xylene and the solutions added to the middle distillate oil to incorporate the additive at various treat rates of additive per thousand barrels of gasoline. The middle distillate samples so treated were then tested for rust according to the NACE Rust Test described in the preceding section on gasoline additives. The results of the test are recorded with the same rating designation as previously set forth, i.e. a rating of A-E which test results are set forth hereafter in Table II.

TABLE II

| Additive | Amine Salt | Middle Distillate A** | | Middle Distillate B*** | |
|---|---|---|---|---|---|
| | | PtB* | NACE Rating | PtB* | Nace Rating |
| — | — | 0 | B+ | 0 | C,D |
| 14B | OSA.DOBO.DETA (3:1) | 1 | A | — | — |
| 15 | OSA.DOBO.EDA (2:1) | 1 | A | 1 | A |
| DCI 6A² | | 2 | B++ | — | — |
| Tolad 244³ | | 1 | B+ | 1 | B++ |
| Tolad 303⁴ | | 1 | B+ | | |

*PTB indicates the number of pounds per thousand barrels.
**Middle Distillate A is a hydrocracked heating oil with a specific gravity of 26.9° API.
***Middle Distillate B is a heating oil having a specific gravity ranging between 28–30° API.
²An additive which consists of about 80% organic acids sold by E. I. duPont of Wilmington, DEL.
³Tolad 244 is commercially available from Petrolite Corp., St. Louis, Missouri.
⁴Tolad 303 is commercially available from Petrolite Corp., St. Louis, Missouri.

The excellent results realized with the additives of the invention in their ability to inhibit corrosion in middle distillates provides a new mechanism for reducing corrosion in tanks containing such middle distillates or pipelines used for transport thereof.

ETHOXYLATED HALF ESTER DERIVATIVES

The foregoing discussion has shown that amine salts of these carboxylate half esters of the aldehyde-THAM adducts have utility as anti-corrosion agents or additives for gasolines and middle distillate fuels. Instead of preparing the amine salts, it is possible to produce ethoxylated derivatives of half ester by reacting one to three moles of an alkylene oxide such as ethylene oxide with each mole of the half ester of the alkenylsuccinic anhydride DOBO adduct. Typical of such ethoxylations are the reaction of one mole of ethylene oxide with one mole of polyisobutenylsuccinic anhydride.DOBO at 100° C. for 2 hours; the reaction of two moles of ethylene oxide with octadecenylsuccinic anhydride.-DOBO at 100° C. for 3½ hours; the products of which individually and collectively exhibited gasoline rust inhibition in the ASTM D 665-M rust test when used in approximately a treat rate of 6 lbs. per thousand barrels. In addition, the ethoxylated material should exhibit effectiveness as a carburetor detergent and as a water shedder for gasoline.

The invention in its broader aspect is not limited to the specific details shown and described and departures may be made from such details without departing from the principles of the invention and without sacrificing its chief advantages.

What is claimed is:

1. A fuel composition comprising a major amount of liquid hydrocarbon fuel and in the range of about 0.001 to 0.5 wt.% of a fuel soluble amine salt-ester wherein said amine contains from 1 to 3 nitrogens and from 2 to 12 carbons and said ester is the half ester reaction product of: (a) about 1 molar proportion of a hydrocarbyl substituted $C_4$ to $C_{10}$ dicarboxylic acid or anhydride having about 2 to about 50 carbon atoms per hydrocarbyl group partly esterified with the reaction product of (b) either about 1 or 2 molar proportions of an aldehyde, or one molar proportion of ketone and one molar proportion of aldehyde, reacted with about 1 molar proportion of tris-(hydroxymethyl) aminomethane; said half ester reaction product having a 1-aza-3,7-dioxabicyclo[3.3.0] octyl ring.

2. A composition according to claim 1, wherein said hydrocarbyl substituted acid or anhydride is alkenyl succinic anhydride.

3. A composition according to claim 2, wherein said alkenyl group is a polymer of a $C_2$ to $C_5$ monoolefin.

4. A composition according to claim 1 wherein said amine salt is the equimolar reaction product of a hydroxy amine having the formula

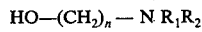

$$HO-(CH_2)_n - N R_1R_2$$

wherein $n$ represents the whole number 2, 3 or 4, $R_1$ and $R_2$ may be the same or different and each represents hydrogen, a hydroxyl alkyl group having 2 to 4 carbons or an alkyl group having 2 to 4 carbons and said half ester reaction product.

5. A composition according to claim 4 wherein said hydroxy amine is ethanolamine.

6. A composition according to claim 1 wherein said amine salt is the equivalent reaction product of an alkylene polyamine of the class consisting of ethylene diamine and diethylene triamine and said half ester reaction product.

7. A composition according to claim 1, wherein said hydrocarbyl group contains about 12 to 24 carbon atoms.

8. A composition according to claim 6, wherein said hydrocarbyl substituted acid or anhydride is octadecenyl succinic anhydride.

9. A composition according to claim 6, wherein said hydrocarbyl substituted acid or anhydride is tetrapropenyl succinic anhydride.

10. A fuel composition comprising a major amount of liquid hydrocarbon fuel and in the range of about 0.001

Finally, a second approach which is also operative in certain cases, simply involves the addition of a carboxylic acid or anhydride to the aldehyde and THAM reagents (in the required molar proportions) and heating the resulting mixture until product formation is complete as discerned by infrared analysis. Example 12 describes briefly the experimental details of this approach.

Example 12

A mixture comprising a tenth mole of paraformaldehyde, 0.05 mole of THAM and 0.05 mole of n-octenylsuccinic anhydride is gradually heated, with stirring, to about 160°–170° C. for about an hour. The infrared spectrum of the reaction product was virtually identical to that recorded for the product obtained in Example 11.

Example 13

AMINE SALTS OF HALF ACID ESTER OF 1-AZA-3,7-DIOXABICYCLO[3.3.0]OCT-5-YL METHYL n-DODECENYLSUCCINATE

A mixture of 0.06 mole (30 g) of the product of Example 2 (OSA-DOBO) and 0.03 mole (1.8 g) of ethylene diamine (EDA) was admixed with 100 ml of tetrahydrofuran (THF) at 36° C. overnight. The THF was removed under vacuum. The reaction product analysis showed 5.58 wt. % nitrogen (Kjeldahl) with calculated N at 7.57%.

Example 14

14A (1:3)

A mixture of 0.06 moles (30 g) of the product of Example 2 (OSA-DOBO) and 0.02 moles (1.2 g) of diethylene triamine (DETA) was admixed with 100 ml THF at 27° C. overnight. The THF was removed under vacuum. The reaction product analyzed at 5.02 wt.% nitrogen (Kjeldahl); calculated 5.28 wt.%.

14B (1:2)

A mixture of 0.06 moles (30 g) of the product of Example 2 (OSA-DOBO) and 0.03 moles (1.8 g) of DETA was admixed with 100 ml THF at 27° C. overnight. The THF was removed under vacuum. The reaction product analyzed at 5.0 wt.% nitrogen (Kjeldahl); calculated 6.4 wt.%.

Example 15

A mixture of 0.06 moles (30 g) of the product of Example 2 (OSA-DOBO) and 0.06 moles of ethanolamine (ETA) was admixed in 100 ml. of THF and stirred overnight at 27° C. The THF was removed under vacuum. The product analyzed at 4.84 wt.% nitrogen (Kjeldahl); calculated 5.03 wt.%.

USE OF THE AMINE SALT-ESTER ADDITIVE IN LIQUID HYDROCARBON FUEL COMPOSITIONS

The amine salt ester reaction products of this invention can be incorporated into a wide variety of fuels for antirust activity.

When the products of this invention are used as multifunctional additives having detergents, antirust properties in petroleum fuels such as gasoline, kerosene, diesel fuels, No. 2 fuel oil and other middle distillates, a concentration of the additive in the fuel in the range of 0.001 to 0.5 weight percent, based on the weight of the total composition, will usually be employed.

These middle distillate fuels are characterized generally by boiling within the range of about 120° to 500° C.

The amine acid salts-ester additives may be conveniently dispensed as an additive concentrate of from 2 wt.% to 100 wt.% with the balance conventionally an oleaginous material such as fuel or a mineral lubricating oil e.g. up to 98 weight percent, with or without other additives being present.

In the above compositions or concentrates, other conventional additives may also be present including dyes, detergents such as the reaction product of an aliphatic polyamine with an alkylated aryl carboxylic acid and antiicing additives, e.g. a hexylene glycol in gasolines and pour point depressants and cold flow improvers for the middle distillate fuels.

GASOLINE ADDITIVES

The products of Examples 13, 14 and 15 were tested for their effectiveness as gasoline antirust agents. Each product was first dissolved in xylene and the solutions added to the gasoline to incorporate the additive at various treat rates of amine salt-half ester additive per thousand barrels of gasoline. The gasoline samples so treated were then tested for rust according to the National Association Corrosion Engineers (NACE) Rust Test (published in U.S. Pat. No. 3,623,851 as the Colonial Pipe Line Rust Test). In brief, this test involves placing 300 ml of the hydrocarbon fuel composition to be tested in a beaker and the stirred composition heated to 38° C. A steel test specimen is inserted into the stirred, heated oil composition where it remains for about 30 minutes to insure complete wetting of the steel specimens by the fuel composition.

To the stirred oil compositions are added 30 ml. of distilled water. The mixture is stirred at 38° C. for an additional 3.5 hours. The steel specimen is then removed, allowed to drain and then washed with precipitation naphtha or isooctane. The percent of the surface of the steel test specimen that is covered by rust is determined. The results are expressed as follows:

| Rating | Percent of Surface Rusted |
|--------|---------------------------|
| A      | None                      |
| B++    | Less than 0.1%            |
| B+     | Less than 5%              |
| B      | 5 to 25%                  |
| C      | 26 to 50%                 |
| D      | 51 to 75%                 |
| E      | 76 to 100%                |

The results of the tests are set forth in Table I.

TABLE I

| Additive of Example | Amine Salt | Concentration Pounds/ Thousand Barrels | NACE Rating |
|---|---|---|---|
| none | — | — | E |
| 2 | OSA.DOBO | 1.25 | A |
|   |          | 0.75 | B+ |
| 13 | OSA.DOBO.EDA (1:2) | 1.0 | A |
|    |                    | 0.75 | B+ |
| 14A | OSA.DOBO.DETA (1:3) | 1.0 | A |
|     |                     | 0.75 | B++ |
|     |                     | 0.5 | B+ |
| 14B | OSA.DOBO.DETA (1:2) | 1.0 | B |
|     |                     | 0.5 | E |
| 15 | OSA.DOBO.ETA | 1.0 | A |
|    |              | 0.75 | A |
|    |              | 0.5 | B++ |
| — | OSA.DOBO.hexylamine | 1.0 | B |
|   |                     | 0.5 | B |
| — | OSA.DOBO.Primene 81R | 3.0 | A |
|   |                      | 1.0 | C | to 0.5 wt.% of a fuel soluble ethoxylated half ester which is the reaction product of: (a) about 1 molar proportion of a hydrocarbyl substituted $C_4$ to $C_{10}$ dicarboxylic acid or anhydride having about 6 to about 50 carbon atoms per hydrocarbyl group partly esterified with the reaction product of (b) either about 1 or 2 molar proportions of an aldehyde, or one molar proportion of ketone and one molar proportion of aldehyde, reacted with about 1 molar proportion of tris(hydroxymethyl) aminomethane; said reaction product having a 1-aza-3,7-dioxabicyclo[3.3.0] octyl ring.

11. A composition according to claim 10 wherein said ethoxylated half ester is the reaction product of one to three moles of ethylene oxide to one mole of said reaction product.

* * * * *